United States Patent [19]

Frigg et al.

[11] Patent Number: 5,041,119
[45] Date of Patent: Aug. 20, 1991

[54] ANGULAR ATTACHMENT FOR DRILL

[75] Inventors: Robert Frigg, Paoli, Pa.; Paul Gisin, Waldenburg; Guido Scandella, Davos, both of Switzerland

[73] Assignee: Synthes, Paoli, Pa.

[21] Appl. No.: 446,041

[22] Filed: Dec. 5, 1989

[30] Foreign Application Priority Data

Jun. 16, 1989 [CH] Switzerland .................. 02222/89

[51] Int. Cl.$^5$ .............................................. A61B 17/16
[52] U.S. Cl. ....................................... 606/96; 606/97; 606/79; 606/80
[58] Field of Search ................ 408/238, 239, 241 G; 211/69; 206/379; 606/33, 54, 80, 96, 97, 98, 79

[56] References Cited

U.S. PATENT DOCUMENTS

| 3,704,707 | 12/1976 | Halloran | 606/97 |
| 3,867,943 | 2/1975 | Nordin | 408/238 X |
| 4,257,411 | 3/1981 | Cho | 606/96 |
| 4,522,201 | 6/1985 | Tongue | 606/65 X |
| 4,541,424 | 9/1985 | Grosse et al. | 606/98 |
| 4,848,327 | 7/1989 | Perdue | 606/54 |
| 4,850,344 | 7/1989 | Olerud et al. | 606/97 |
| 4,901,711 | 2/1990 | Goble et al. | 606/97 |
| 4,917,111 | 4/1990 | Pennig et al. | 606/97 |

Primary Examiner—Robert A. Hafer
Assistant Examiner—Kerry Owens
Attorney, Agent, or Firm—Davis Hoxie Faithfull & Hapgood

[57] ABSTRACT

An angle frame for surgical use is made of materials permeable by X-radiation.

3 Claims, 1 Drawing Sheet

ANGULAR ATTACHMENT FOR DRILL

FIELD OF THE INVENTION

This invention relates to an angle frame or angular drilling attachment for a drilling machine used for surgical purposes and to a surgical method for drilling a hole in a bone with X-ray guidance using an angular drilling attachment.

BACKGROUND OF THE INVENTION

Drilling machines are used in a number of surgical procedures, for example, in making holes in bones for bone screws and in drilling out the medulla or marrow areas of bones. In the latter procedure, in particular, it is normally necessary to use an angle frame, i.e., a device which will translate the rotation of the drilling machine to turn a drill having an axis at an angle to the axis of rotation of the drilling machine. Such devices are known and are commercially available.

To improve the precision of surgical drilling, a technique has been developed in recent years in which the bone is positioned in the path of radiation from an X-ray machine with video amplifier control. Various types of aiming devices can be used to verify and monitor the position and direction of the drill bit. See, for example, Frigg et al., U.S. Pat. No. 4,803,976.

Such aiming devices have suffered from the disadvantage that during the actual drilling procedure the position of the drill bit cannot be observed directly because the drilling machine covers the visual field of the video amplifier. A further disadvantage of covering the field of vision is that the automatic control of radiation by the amplifier raises the radiation intensity to penetrate the metal of the drilling machine. This increased radiation naturally also affects the hand of the surgeon guiding the drilling machine. Secondary radiation occurring through reflection from the metal is of particular danger.

SUMMARY OF THE INVENTION

The foregoing problems are overcome according to the invention, in a process for drilling a hole in a bone in which the position of a metallic drill bit is monitored by X-radiation by holding the drill bit in an angular drilling attachment made at least in large part of a material which is penetratable by X-radiation.

The invention further comprises an angular drilling attachment for use in surgical, and in particular, in osteosynthetic procedures having a housing with a front end and a rear end, means for securing the rear end to a drilling machine and means for securing a drill bit at the front end of said housing, the means for securing the drill bit being constructed of a material penetratable by X-radiation.

BRIEF DESCRIPTION OF THE DRAWING

The single figure of the drawing shows an angular drilling attachment according to the invention with portions of a drilling machine and drill bit in position.

DESCRIPTION OF A SPECIFIC EMBODIMENT

Figure 1:
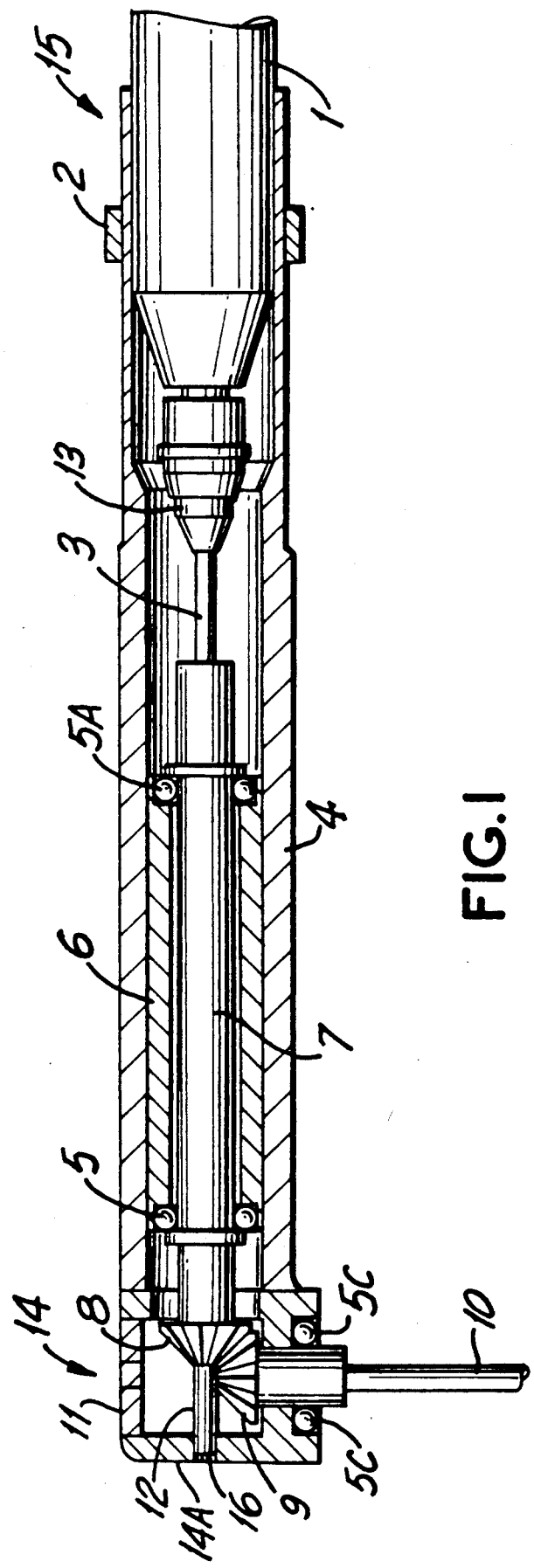

Referring to the drawing an angular drilling attachment according to the invention comprises a housing 4 having a front end 14 and a rear end 15. The rear end is tubular, tapered somewhat and open to receive the working end of a drilling machine 1. A retaining ring 2 is located on the outside of the rear end of the housing to secure the housing to the drilling machine.

The drilling machine, which may be of any conventional type has a chuck 13 which engages a coupling shaft 3 which in turn is attached to a drive shaft 7 of the frame. The drive shaft 7 is positioned in a bearing cage 6 having a front ring bearing 5 and a rear ring bearing 5A. At its front end drive shaft 7 has a first conical gear 8 which engages a second conical gear 9 at right angles thereto. The second conical gear 9 drives drill bit 10. The conical gear 9 can be secured directly to the drill bit 10 or made in the form of a chuck. The latter variation is not shown.

Drive shaft 7 is stabilized by a support pin 12 which is supported in a socket 16 in the front end wall 14A of the angle frame. Bearings 5C are provided to accommodate rotation of the drill bit 10. The support pin 12 is not absolutely necessary and can be replaced by an extension of the drill bit 10 to the housing cover 11.

This last embodiment, which is not shown, enables a hollow drill bit to be used where it is to be inserted over a guide or spike wire. The spike wire performs the function of a probe, which can be positioned in optimal manner, possibly after several attempts, and which guides the drill bit 10 during the actual drilling process. This drilling technique is used, for example, on the spinal column or the pelvis, where bone screws must be set with extreme precision.

Even where guide wires are used, the drilling process is done with video amplifier monitoring; the reason for this is the danger of an advance by the spike wire and the lateral penetration of the drill bit 10 out of the bone. In such drilling, particularly on the spinal column, the X-ray penetrability of the angular drilling attachment is extremely helpful, because there is no resulting darkening or irradiation of the video amplifier picture, so that on the one hand the vertebral body to be drilled remains clearly visible, and on the other hand the drilling procedure can be monitored.

In accordance with the invention, all parts of the angular drilling attachment, with the possible exception of locking ring 2 and coupling 3 are made of a material which is penetratable by X-radiation. Such material may be any of a variety of suitable materials, such for example, as a synthetic resin or certain ceramics. It is desirable that the material be capable of sterilization by heat and hence that it have high temperature resistance. For this reason synthetic resins such as polyacetals, for example, formaldehyde polymers and copolymers such as Delrin and Celcon, and polyether ether ketones are particularly useful. Composite materials, i.e., synthetic resins reinforced by fibers, webbing or pellets, such as graphite/epoxy composites, as well as special ceramic materials can also be used.

What is claimed is:

1. An angular attachment for a surgical drilling machine comprising a tubular housing with a front end and a rear end, a drill bit, means for securing said drill bit to the front end and means for securing the rear end to a drilling machine, at least said front end and said means for securing a drill bit being constructed of a material penetrable by x-radiation, a drive shaft having an axis of rotation, means for attaching said drive shaft to the drilling machine, and connecting means for connecting said drive shaft to said drill bit to rotate said drill bit at an angle to the axis of said drive shaft, said connecting means comprising two intermeshing conical gears.

2. The attachment claimed in claim 1 wherein said drive shaft and connecting means are made of an X-radiation permeable material.

3. The attachment claimed in claim 1 and comprising a support bolt coaxial with said drive shaft for stabilizing said drive shaft, said support bolt being made of a material permeable by X-radiation.

* * * * *